[19] United States Patent
Weber et al.

[11] Patent Number: 4,670,456
[45] Date of Patent: Jun. 2, 1987

[54] 4-AMINOCARBONYLAMINOMETHYL-1-BENZYLPYRROLIDIN-2-ONES AS NOOTROPIC AGENTS AND AS AGENTS FOR TREATING CEREBRAL INSUFFICIENCY

[75] Inventors: Karl-Heinz Weber, Gau-Algesheim; Claus Schneider, Ingelheim an Rhein; Gerhard Walther, Bingen am Rhein; Dieter Hinzen, Bingen; Franz J. Kuhn, Gau-Algesheim; Erich Lehr, Waldalgesheim; Helmut Ensinger, Wackernheim; Wolfgang Tröger, Stromberg, all of Fed. Rep. of Germany

[73] Assignee: Boehringer Ingelheim KG, Ingelheim am Rhein, Fed. Rep. of Germany

[21] Appl. No.: 738,152

[22] Filed: May 24, 1985

[30] Foreign Application Priority Data

May 30, 1984 [DE] Fed. Rep. of Germany ....... 3420193

[51] Int. Cl.$^4$ .................. A61K 31/40; C07D 207/12
[52] U.S. Cl. ................... 514/424; 514/214; 514/234; 514/252; 514/326; 514/343; 540/585; 544/131; 544/141; 544/372; 546/193; 546/208; 546/281; 548/518; 548/550
[58] Field of Search ....... 548/518, 523, 550; 514/315, 318, 343, 424; 544/131

[56] References Cited

U.S. PATENT DOCUMENTS 3,459,738  8/1969  Morren ............................ 260/239.3
4,369,139  1/1983  Kyburz et al. .................... 548/524

FOREIGN PATENT DOCUMENTS 165919  10/1985  European Pat. Off. ............ 548/550
2140694  2/1972  Fed. Rep. of Germany ...... 548/550
39-26970 11/1964  Japan .............................. 548/550
41-2628  2/1966  Japan .............................. 548/550
3044559  4/1978  Japan .............................. 548/550
3065873  6/1978  Japan .............................. 548/550
8065272  4/1983  Japan .............................. 548/550
629771  5/1982  Switzerland .
1309692  3/1973  United Kingdom ............... 548/550

OTHER PUBLICATIONS

U.S. Ser. No. 657,219, Weber et al., filed 10-3-1984; and U.S. Ser. No. 678,739, filed 7-9-1984.
B. R. J. Nicholaus, Drug. Dev. Res. 2, 463–474 (1982).
R. Cumin et al, Psychopharmacology, 78, 104–111 (1982).
T. M. Itil et al, Psychopharmacology Bulletib, 19/4, 708–716 (1983).
B. P. H. Poschel et al, Psychopha–macology Bulletin, 19/4, 720–721 (1983).
T. A. Pugsley et al, Psychopharmacology Bulletin, 19/4, 721–726 (1983).
R. J. Branconnier et al, Psychopharmacology Bulletin, 19/4, 726–730 (1983).
Stratford et al, J. Med. Chem., 26 pp. 1463–1469 (1983).

Primary Examiner—Robert Gerstl
Assistant Examiner—C. Shen
Attorney, Agent, or Firm—David E. Frankhouser; Alan R. Stempel

[57] ABSTRACT

The invention relates to new substituted pyrrolidinones of general formula

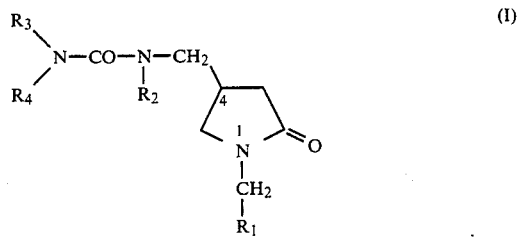

wherein
$R_1$ represents a phenyl group which may be mono- or di-substituted by methyl, methoxy, fluorine, chlorine, bromine or trifluoromethyl, or a pyridyl group;
$R_2$ represents hydrogen or a straight-chained or branched alkyl group with 1–4 carbon atoms;
$R_3$ represents a straight-chained or branched alkyl group with 1–3 carbon atoms, a hydroxyalkyl group with 2–3 carbon atoms, a phenyl group which can be mono- or di-substituted by chlorine, bromine, methyl or methoxy, a cyclohexyl group or a dialkylamino alkyl group, where in each alkyl group can contain from 1–3 carbon atoms;
$R_4$ represents hydrogen or a straight-chained or branched alkyl group with 1–3 carbon atoms; or
$R_3$ and $R_4$ together with the nitrogen atom represent a piperidine, morpholine or piperazine ring, while the ring may be substituted by 1 or 2 methyl groups and the piperazine ring at the nitrogen atom in 4-position may also carry a phenyl, chlorophenyl or benzyl group, or they may represent the nortropanyl group, processes for preparing them and pharmaceutical compositions.

The new compounds have proved effective in animal trials in alleviating or remedying conditions or restricted cerebral performance.

6 Claims, No Drawings

4-AMINOCARBONYLAMINOMETHYL-1-BEN-ZYLPYRROLIDIN-2-ONES AS NOOTROPIC AGENTS AND AS AGENTS FOR TREATING CEREBRAL INSUFFICIENCY

BACKGROUND OF THE INVENTION

1. Field of the Invention

The invention relates to new substituted pyrrolidinones, processes for preparing them and the use of these compounds as nootropic agents or as agents for treating cerebral insufficiency.

2. Description of Related Art

The nootropics are a relatively recently recognized class of therapeutic agents which have been described in the literature [B. J. R. Nicolaus, Drug Dev. Res. 2, 463–474 (1982)] as acting on the cerebral cortex and being characterized as having activator, protective, and function restoring effects on nerve cells in distress. Further, according to this reference, the nootropics do not possess sedative or stimulating effects and do not influence behavior, and thus differ substantially from the psychotropic agents.

The literature describes a number of the known nootropic compounds, most notably 1-carbomyl-methyl-pyrrolidin-2-one (piracetam), 1-(p-methoxybenzoyl)-pyrrolidin-2-one (anirazetam, RO 13-5057) and 1-carbamoylmethyl-4-hydroxy-pyrrolidin-2-one (oxiracetam).

DESCRIPTION OF THE INVENTION

The compounds of the present invention are also pyrrolidinone derivatives and are useful as nootropic agents, but unlike the prior art compounds, they contain a side chain with an amino carbonyl function. It has been found that the introduction of this group brings about a substantial improvement in activity compared with the known substances.

More specifically, the compounds provided by the invention are pyrrolidinones of the formula

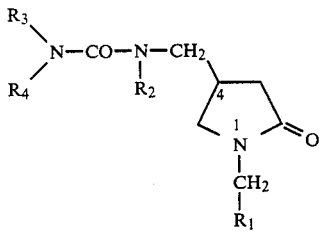

(I)

wherein
R$_1$ is a phenyl group which may be mono- or di-substituted by methyl, methoxy, fluorine, chlorine, bromine or trifluoromethyl, or a pyridyl group;
R$_2$ is hydrogen or a straight-chained or branched alkyl group with 1–4 carbon atoms;
R$_3$ is a straight-chained or branched alkyl group with 1–3 carbon atoms; a hydroxyalkyl group with 2–3 carbon atoms; a phenyl group which can be mono- or di-substituted by chlorine, bromine, methyl or methoxy; a cyclohexyl group or a dialkylaminoalkyl group, wherein each alkyl group can contain from 1–3 carbon atoms;
R$_4$ is hydrogen or a straight-chained or branched alkyl group with 1–3 carbon atoms; or,
R$_3$ and R$_4$ together with the nitrogen atom are a piperidine, morpholine or piperazine ring, which ring can be substituted by 1 or 2 methyl groups and, in the case of piperazine, can also be substituted at the 4-position nitrogen atom with a phenyl, chlorophenyl or benzyl group, or R$_3$ and R$_4$ taken together can be the nortropanyl group.

Compounds of the above formula I which have a basic function therin can form physiologically acceptable acid addition salts. Suitable acids for this purpose are both inorganic acids such as hydrohalic acids, sulphuric, phosphoric and aminosulphonic acids and also organic acids such as formic, acetic, propionic, lactic, glycolic, gluconic, maleic, fumaric, succinic, tartaric, benzoic, salicylic, citric, ascorbic, p-toluenesulphonic or hydroxyethanesulphonic acid. Conversion into the acid addition salts is carried out by conventional methods.

Preferred compounds of formula I are those wherein R$_1$ is a phenyl group; R$_2$ is hydrogen; R$_3$ is a phenyl group which is optionally chlorine-substituted in the o- and/or p-position or, R$_3$ together with R$_4$ and the nitrogen atom is a basic group; and, R$_4$ is hydrogen. Of particular interest are those compounds of formula I wherein R$_1$ is phenyl, R$_2$ is hydrogen, R$_3$ is p-chlorophenyl and R$_4$ is hydrogen or R$_3$ and R$_4$ together with the nitrogen atom are a piperazine ring which is optionally methyl substituted in the 4-position. Particular mention should be made of the compounds 4-(N-methylpiperazinyl-carbonylaminomethyl)-1-benzylpyrrolidin-2-one and 4-(p-chlorophenylamino-carbonylaminomethyl)-1-benzlpyrrolidin-2-one.

The invention further relates to the following processes for preparing compounds of formula I which comprise:

(a) reacting an aminomethylpyrrolidin-2-one of the formula

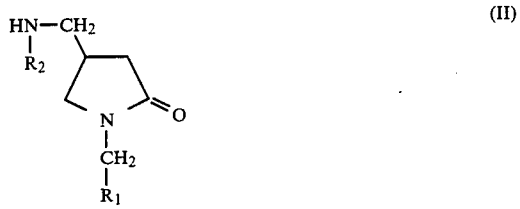

(II)

wherein
R$_1$ and R$_2$ are as hereinbefore defined, with an isocyanate of the formula

O=C=N—R$_3$ (III)

wherein
R$_3$ is as defined hereinbefore, with the exception of the hydroxyalkyl group, in order to yield a compound of formula I wherein R$_4$ is hydrogen, or (b) reacting a compound of formula II with a chlorocarbonylamide of the formula

(IV)

wherein
R$_3$ is as defined hereinbefore, with the exception of hydroxyalkyl, and R$_4$ is as defined hereinbefore with the exception of hydrogen, or (c) reacting a compound of formula II with a chlorocarbonate of the formula $$Cl-CO-O-Y \quad (V)$$

wherein

Y is an alkyl group with 1-4 carbon atoms or a benzyl, phenyl or p-nitrophenyl group, to yield a carbamate of the formula

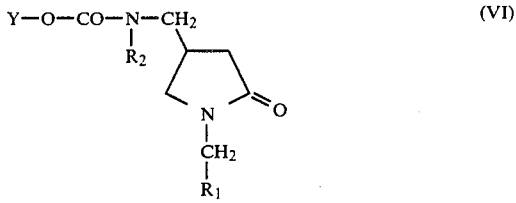
$$(VI)$$

wherein $R_1$, $R_2$ and Y are as hereinbefore defined, and thereafter reacting the carbamate VI with an amine of the formula

$$(VII)$$

wherein $R_3$ and $R_4$ are as hereinbefore defined, to yield the desired end product, or (d) alkylating an end product of formula I wherein $R_2$ and/or $R_4$ represent hydrogen.

Processes (a) and (b) are carried out in inert anhydrous solvents such as dioxane, tetrahydrofuran, dimethylformamide, ether, benzene, toluene, chlorinated hydrocarbons and the like, at temperatures of between 0° C. and the boiling temperature of the reaction mixture. The reactions are preferably carried out at ambient temperature. The reaction of an amino compound of formula II with an isocyanate of formula III may also be carried out without a solvent. In process (b) it is advisable to add an acid-binding agent, e.g. an organic base such as triethylamine or pyridine or an alkali metal carbonate.

In the two-step process (c) the first step, namely the reaction of an amine of formula II with a chlorocarbonate of formula V, is carried out in an anhydrous inert slvent, such as those mentioned above, and at a temperature between 0° C. and the boiling temperature of the reaction mixture.

The reaction between a carbamate of formula VI formed as an intermediate and an amine of formula VII is carried out in anhydrous inert solvents such as those mentioned above by way of example or with an excess of the amine of formula VII, at a temperature between 0° C. and ambient temperature or a moderately elevated temperature. In the case of low-boiling amines it is advisable to use an autoclave. If desired, a tertary organic base may be added to the reaction in order to trap the phenol formed.

The alkylation mentioned in (d) is carried out in a conventional manner by salt formation at the urea using sodium hydride or sodium methoxide with subsequent reaction with an alkylhalide or a dialkylsulphate.

The compounds of formula I have a center of asymmetry and are therefore obtainable as racemates. These racemates can be converted in the usual way, e.g. by salt formation with optically active acids, into the corresponding diastereomers, which may then be converted into the optically active end products.

The optically active end products can also be obtained directly from optically active aminoalkyl compounds of formula II.

Processes for preparing the 4-aminomethylpyrrolidinones of formula II used as starting materials are described in German Patent Application No. P 33 36 024.3. These compounds can be obtained, for example, starting from a 4-cyanomethylaminopyrrolidin-2one, correspondingly substituted at the nitrogen atom, by hydrogenation in a conventional manner.

The following end products, for example, may be obtained using the processes described hereinbefore:

4-(methylamino-carbonylaminomethyl)-1-benzylpyrrolidin-2-one, 4-(isopropylamino-carbonylaminomethyl)-1-benzylpyrrolidin-2-one, 4-(N,N-dimethylaminoethylamino-carbonylaminomethyl)-1-benzylpyrrolidin-2-one, 4-(cyclohexylamino-carbonylaminomethyl)-1-benzylpyrrolidin-2-one, 4-(m-chlorophenylamino-carbponylaminomethyl)-1-benzylpyrrolidin-2-one, 4-(N-nortropanyl-carbonylaminomethyl)-1-benzylpyrrolidin-2-one 4-(N-morpholino-carbonylaminomethyl)-1-(p-methoxybenzyl)pyrrolidin-2-one, 4-(N-methylpiperazinyl-carbonylaminomethyl)-1-benzylpyrrolidin-2-one, 4-(N-methylpiperazinyl-carbonylaminomethyl)-1-(p-methylbenzyl)pyrrolidin-2-one, 4-(2,6-dimethylmorpholino-carbonylaminomethyl)-1-(p-methylbenzyl)-pyrrolidin-2-one, 4-(N-methylpiperazinyl-carbonylaminomethyl)-1-(o-chlorobenzyl)pyrrolidin-2-one, 4-(N-methylpiperazinyl-carbonylaminomethyl)-1-(p-fluorobenzyl)pyrrolidin-2-one, 4-(N-methylpiperazinyl-carbonyl-N'-methyl-aminomethyl)-1-benzylpyrrolidin-2-one, 4-(N-methylpiperazinyl-carbonyl-N'-isopropyl-aminomethyl)-1-benzylpyrrolidin-2-one, 4-(N-dimethylamino-carbonyl-N'-isopropyl-aminomethyl)-1-benzylpyrrolidin-2-one, 4-(morpholino-carbonylaminomethyl)-1-benzylpyrrolidin-2-one, 4-(piperazino-carbonylamiomethyl)-1-benzylpyrrolidin-2-one, 4-(N-chlorophenyl)-piperazino-carbonylaminomethyl)-1-benzylpyrrolidin-2-one, 4-(piperidino-crbonylaminomethyl)-1-benzylpyrrolidin-2-one, 4-(β-hydroxyethylamino-carbonylaminomethyl)-1-benzylpyrrolidin-2-one, 4-(p-chlorophenylamino-carbonylaminomethyl)-1-benzylpyrrolidin-2-one, 4-(N-benzylpiperazinyl-carbonylaminomethyl)-1-benzylpyrrolidin-2-one.

The pharmacology of the compounds of formula I has been investigated through the use of several animal experiments.

As described more fully in Example 8 herein, the compounds tested showed no acute toxicity in the mouse over a 14 day observation period, at dosages of up to 2 g/kg, given as a single oral dose.

Also as described in Example 8, the compounds tested bound with high affinity to muscarine-cholinergic receptor structures in the rat cortex.

In tests on central activation, desynchronization was found (waking or conscious reactions) in the EEG of rabbits treated with those compounds so tested.

The learning capacity of rats in an active avoidance training [J. Pharmacol. Methods, 8, 255–263 (1983)] has been found to be improved by the administration of compounds of formula I, as is their habituation or exploratory orientation activities in a new environment.

As is more fully described in Example 8, compounds of formula I have also been shown, in the "Reversal of Scopolamine—Induced Transient Disruption of Memory Test" and the "Hypoxia Tolerance Test", to be capable of counteracting experimentally induced cerebal insufficiency in laboratory animals. Further, the compounds of formula I so desired have been found to be substantially more active than the known nootropics Piracetam and Aniracetam when tested in the same manner.

As mentioned above, the compounds of the invention are nootropic agents and are useful for treating conditions of cerebral insufficiency, that is to say, conditions characterized by restricted or imparied cerebral performance such as learning and memory. The mode of using the compounds provided will be qualitatively similar to that employed with known, structurally related nootropics.

A suitable dosage for a compound of formula I would be 25–100 mg per dosis for oral administration or 5–25 mg per dosis for parenteral administration, there being three administrations per 24 hour period. It should be understood, however, that the dosage administration from patient to patient will vary and the dosage for any particular patient will depend upon the judgement of the clinician, who will use as criteria for fixing a proper dosage the size and condition of the patient as well as the patient's response to the drug.

The new compounds may be used either alone or in combination with each other, as well as in combination with other pharmacologically active substances, e.g. other cerebral activators. Suitable forms for administration include, for example, tablets, capsules, suppositories, solutions, syrups, emulsions or dispersible powders. Corresponding tablets may be obtained, for example, by mixing the active substance or substances with known excipients, e.g. inert diluents such as calcium carbonate, calcium phosphate or lactose, disintegrants such as corn starch or algenic acid, binders such as starch or gelatine, lubricants such as magnesium stearate or talc, and/or agents for obtaining delayed release such as carboxypolymethylene, carboxymethylcellulose, cellulose acetate phthalate, or polyvinylacetate. The tablets may also consist of several layers.

Coated tablets may be prepared analogously by coating cores produced in the same way as the tablets with the substances normally used for tablet coatings, e.g. collidone or shellac, gum arabic, talc, titanium dioxide or sugar. In order to achieve delayed release or avoid incompatibilities the core may also consist of several layers. Similarly, the tablet coating may consist of several layers in order to obtain a delayed release, while the excipients mentioned above for the tablets may be used.

Syrups of the active substances or combinations of active substances according to the invention may additionally contain a sweetener such as saccharin, cyclamate, glycerine or sugar and a flavor-improving agent, e.g. flavorings such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. by employing a conventional pharmaceutically acceptable liquid carrier, such as sterile water, t which these may be added preservatives such as p-hydroxy-benzoates, or stabilizers such as alkali metal salts of ethylene diamine tetraacetic acid, and then transferring the solution so prepared into injection vials of ampules.

Capsules can be prepared by mixing the active substances with inert carriers such as lactose or sorbitol and packing this mixture into gelatin capsules.

Suitable suppositories may be obtained, for example, by mixing the active substance with suitable carriers, such as neutral fats or polyethylene glycol or derivatives thereof.

The following Examples are intended to further illustrate the invention.

EXAMPLE 1

4-(N-Methylpiperazinyl-carbonylaminomethyl)-1-benzylpyrrolidin-2-one (according to process (b))

36 g (0.18 mol) of 4-Aminomethyl-1-benzylpyrrolidin-2-one, prepared as set forth in German Patent Application No. P 33 36 024.3, are dissolved in 500 ml of dry dioxane and 29 g (0.18 mol) chlorocarbonylmethylpiperazine are added thereto over a period of 30 minutes with stirring. The mixture is refluxed for 30 minutes, during which a dark oil is precipitated. The reaction mixture is concentrated by evaporation and the residue is made alkaline with 2N sodium hydroxide solution while cooling with ice. The title compound is extracted with methylene chloride and, after the solvent has been distilled off, about 50 g of crude product are obtained. After chromatography over $SiO_2$ (eluant methylene chloride/methanol 98:2) and recrystallization from a little ethyl acetate, 42 g of colorless crystals are obtained, m.p. 123°–124° C.

33 g (0.1 mol) of the base are dissolved with 280 ml of hot ethanol and 11.5 g of fumaric acid are added. The fumarate crystallizes out, is cooled and then suction filtered and washed with cold ethanol. Upon drying, the yield is 41 g, m.p. 182°–184° C. The salt contains an equimolar amount of fumaric acid.

EXAMPLE 2

(+)4-(N-Methylpiperazinyl-carbonylaminomethyl)-1-benzylpyrrolidin-2-one

Using the procedure described in Example 1, the title compound is obtained as a colorless oil, $\alpha^{20}+1.8°$ (c=10.0, methanol) in a yield of 40 g, starting from 36 g (0.18 mol) of (−)4-aminomethyl-1-benzylpyrrolidin-2-one (prepared from the racemate by separation of the enantiomers using tartaric acid, $\alpha^{20}-2.1°$ C., c=10.0, methanol) and purified by column chromatography ($SiO_2$, eluant: methylene chloride/methanol 9:1).

By reacting the optically active base with fumaric acid, 48 g of fumarate are obtained, m.p. 179°–180° C. The salt contains an equimolar amount of fumaric acid.

EXAMPLE 3

(−)4-(N-Methylpiperazinyl-carbonylaminomethyl)-1-benzylpyrrolidin-2-one

Starting from (+)4-aminomethyl-1-benzylpyrrolidin-2-one ($\alpha^{20}+2.07°$; c=10.0, methanol) the title compound is obtained in a manner analogous to that used in Example 2, $\alpha^{20}-1.8°$ (c=10.0, methanol). The fumarate is also obtained in a manner analogous to that of Example 2, m.p. 178°–180° C.

EXAMPLE 4

4-(N-Methylpiperazinyl-carbonylaminomethyl)-1-benzylpyrrolidin-2-one (according to process (c))

76 g (0.37 mol) of 4-aminomethyl-1-benzylpyrrolidin-2-one are dissolved in 1.2 liters of dry dioxane and 52 ml of triethylamine are added. 40 ml of phenyl chloroformate are added dropwise thereto, over a period of 15 to 20 minutes, while cooling with ice, and the mixture is evaporated in vacuo after a further 30 minutes. The residue is taken up in methylene chloride and the organic solution is washed several times with water. The dried organic phase is suction filtered over charcoal and evaporated. When ether is added, 100 g of 4-phenoxycarbonylaminomethyl-1-benzylpyrrolidin-2-one crystallizes out, m.p. 89°–90° C.

100 g of this compound are refluxed with 1.2 liters of acetonitrile and 62 g of N-methylpiperazine for 2 hours. The solvent is evaporated off, the product is taken up in methylene chloride, washed with water, and dried with magnesium sulphate, the solvent is evaporated again and the product recrystallized from ethyl acetate. The yield is 78 g, m.p. 124°–126° C.

EXAMPLE 5

4-(p-Chlorophenylamino-carbonylaminomethyl)-1-benzylpyrrolidin-2-one (according to process (a))

52 g (0.25 mol) of 4-aminomethyl-1-benzylpyrrolidin-2-one are stirred for 2 hours at ambient temperature in 70 ml of dioxane with 38 g (0.25 mol) of p-chlorophenylisocyanate and the solution is then evaporated in vacuo. The residue crystallizes out of ethyl acetate to yield 67 g of the title compound, m.p. 139°–140° C.

EXAMPLE 6

4-(N-Methylpiperazinyl-carbonyl-N'-methylaminomethyl)-1-benzylpyrrolidin-2-one (according to process (d))

33 g (0.1 mol) of 4-(N-methylpiperazinyl)-carbonylaminomethyl-1-benzylpyrrolidine-2-one, 500 ml of tetrahydrofuran and 4.5 g of sodium hydride (55% oil suspension) are stirred for 30 minutes at ambient temperature, during which time hydrogen gas is developed. 20 g of methyl iodide are added (about 0.15 mol) and the mixture is refluxed for 3 hours. Then the reaction mixture is concentrated by evaporation, water is added to the residue and this is then extracted with methylene chloride.

The title compound is obtained in a yield of 16 g, m.p. 134°136° C.

EXAMPLE 7

The compounds listed in the following Table I were prepared by processes analogous to those described in Examples 1–6.

TABLE I

[Structure: pyrrolidin-2-one with N—CH$_2$—R$_1$ and CH$_2$—A substituents]

| R$_1$ | A | Mp. Base °C. | Fumarate °C. |
|---|---|---|---|
| 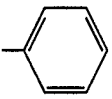 | —N(H)—CO—N(H)—CH$_3$ | 117–118 | |
| 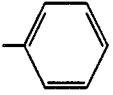 | —N(H)—CO—N(H)—(cyclohexyl) | 115–117 | |
| 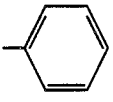 | —N(H)—CO—N(H)—CH(CH$_3$)$_2$ | 102–103 | |
| 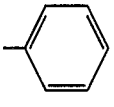 | —N(H)—CO—NH—(3-chlorophenyl) | 114–116 | |

TABLE I-continued
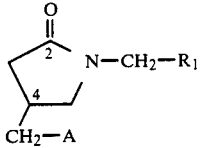
| R₁ | A | Mp. Base °C. | Fumarate °C. |
|---|---|---|---|
| 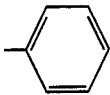 |  | 115–117 | |
| 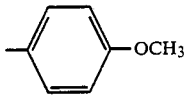 –OCH₃ |  | 104–106 | |
| 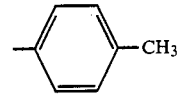 –CH₃ |  | 139–140 | |
| 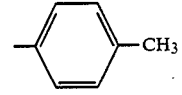 –CH₃ |  | 110–112 | |
| 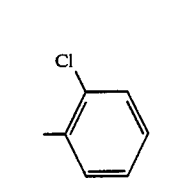 |  | | 178–180 |
|  –F |  | | 153–154 |
| 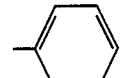 |  | 134–136 | |
| 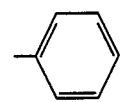 |  | 160–162 | |
| 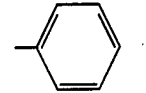 |  | 88–89 | |
| 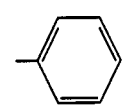 |  | 127–128 | |

TABLE I-continued

Structure:
$$\underset{CH_2-A}{\overset{O}{\underset{4}{\underset{\|}{C}}}}\underset{}{\overset{2}{N}}-CH_2-R_1$$

| $R_1$ | A | Mp. Base °C. | Fumarate °C. |
|---|---|---|---|
| phenyl | −N(H)−CO−N(piperazinyl)NH | Oil | |
| phenyl | −N(H)−CO−N(piperazinyl)−C6H4−Cl | 168–170 | |
| phenyl | −N(H)−CO−N(piperidinyl) | 106–108 | |
| phenyl | −N(H)−CO−N(H)−CH2−CH2−OH | Oil | |
| phenyl | −N(H)−CO−N(piperazinyl)N−CH2−C6H5 | 139–141 | |
| 4-methoxyphenyl | −N(H)−CO−N(piperazinyl)N−CH3 | 114–115 | |
| phenyl | −N(H)−CO−N(2,6-dimethylpiperidinyl) | 131–134 | |

EXAMPLES OF PHARMACEUTICAL FORMULATIONS

| (A) Tablets | per tablet |
|---|---|
| Active substance | 100 mg |
| Lactose (powdered) | 140 mg |
| Corn starch | 240 mg |
| Polyvinylpyrrolidone | 15 mg |
| Magnesium stearate | 5 mg |
| | 500 mg |

The finely ground active substance, lactose, and some of the corn starch are mixed together. The mixture is sieved, then moistened with a solution of polyvinylpyrrolidone in water, kneaded, wet-granulated and dried. The granules, the remaining corn starch and the magnesium stearate are sieved and mixed together. The mixture is compressed to form tablets of suitable shape and size.

| (B) Tablets | per tablet |
|---|---|
| Active Substance | 80 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is sieved and processed with the remaining corn starch and water to form a granulate which is dried and sieved. The sodium carboxymethyl starch and the magnesium stearate are added, mixed together and the mixture is compressed to form tablets of a suitable size.

| (C) Ampules | |
|---|---|
| 4-(N—Methylpiperazinyl-carbonylaminomethyl)-1-benzylpyrrolidin-2-one-fumarate | 50.0 mg |
| Sodium chloride | 10.0 mg |
| doubly distilled water q.s. ad | 1.0 ml |

Preparation

The active substance and the sodium chloride are dissolved in doubly distilled water and the solution is transferred into ampules under sterile conditions.

| (D) Drops (for oral administration) | |
|---|---|
| 4-(Isopropylamino-carbonylaminomethyl)-1-benzylpyrrolidin-2 one fumarate | 5.0 g |
| methyl p-hydroxybenzoate | 0.1 g |
| propyl p-hydroxybenzoate | 0.1 g |
| demineralized water q.s. ad | 100.0 ml |

Preparation

The active substance and preservatives are dissolved in demineralized water and the solution is filtered and transferred into vials containing 100 ml.

EXAMPLE 8

The title compounds of Examples 1, 5, 7, 13 and 17 were subjected to the pharmacological tests described below. For the purpose of comparison, the known nootropics Piracetam and Aniracetam were also subjected to some or all of these tests. The results of the tests performed are given in the following Table II.

1. Reversal of Scopalomine-Induced Transient Disruption of the Memory of a Passive Avoidance Procedure This test is used to access the degree to which a test compound is able to block or otherwise remedy the disruption of the memory of a passive avoidance procedure, which disruption of memory is brought about by administering the muscarinic cholinergic antagonist scopolamine to test animals after they have learned the procedure.

The test procedure employed was substantially that described by Cumin et al., Psycholpharmacology, 78, 104-111 (1982). The animals used were mice, to which scopolamine was administered at a dosage of 0.6 mg/kg, i.p.

2. Hypoxia Tolerance Test

This test is used to assess the ability of a test compound to protect a test animal from sustaining lethal brain damage from experimentally induced hypoxia.

In the the method employed, mice which are untreated controls or which have been pretreated with the test substance (p.o.) are placed in respective sealed chambers which are filled with a gas mixture consisting of 96.5% nitrogen and 3.5% oxygen. The observer waits until 7-8 of the untreated animals have died. This occurs within 6-7 minutes. If the test substance is effective, at most 1-2 of the treated animals may have died.

3. Muscarine-Cholinergic Receptor Binding

This test was performed according to the methods described by M. Watson et al., Life Sci., 32, 3001-3011 (1983) and R. Hammer et al., Nature, 283, 90=92 (1980). The $IC_{50}$ values were calculated in the manner described by Y. C. Cheng et al., Biochemical Pharmacology, 22, 3099-3108 (1973).

4. Acute Toxicity ($LD_{50}$)

The acute toxicity of the test compounds was determined in the conventional manner, in the mouse.

TABLE II

| Title Compound of Example | Scopalamine-Induced Memory Disruption | | Hypoxia Tolerance | Muscarine Receptor Binding mol/l; $IC_{50}$ | | Acute Toxicity ($LD_{50}$) (p.o.) |
|---|---|---|---|---|---|---|
| | mg/kg (p.o.) | % Inhibition | mg/kg (p.o.) | Hippocampus | mg/kg, Cortex | |
| 5 | 5 | 50 | 100 | $9.3 \times 10^{-5}$ | — | >2000 |
| | 10 | 70 | effective | | | |
| 1 | 10 | 43 | 100 | $7.05 \times 10^{-6}$ | $2.76 \times 10^{-6}$ | 1500-2000 |
| | | | effective | | | |
| 7 | 100 | 60 | — | $>10^{-4}$ | — | — |
| 13 | 50 | 50 | — | $2.6 \times 10^{-5}$ | $>10^{-5}$ | — |
| 17 | 30 | 45 | — | $>10^{-4}$ | — | — |
| Piracetam | 100 | 42.9 | 150 | ineffective up to $10^{-3}$ | | — |
| | 200 | 53.7 | effective | | | |
| | 500 | 50.0 | | | | |
| Aniracetam | 30 | 29.7 | — | ineffective up to $10^{-4}$ | | |
| | 50 | 42.6 | | | | |
| | 100 | 49.3 | | | | |

What is claimed is:

1. Substituted pyrrolidinones of the formula

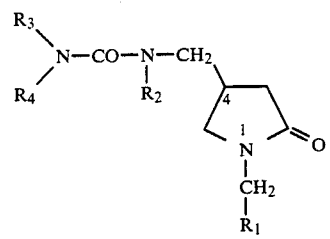

(I)

wherein $R_1$ is a phenyl group which can be mono- or di-substituted by methyl, methoxy, fluorine, chlorine, bromine or trifluoromethyl, or a pyridyl group;

$R_2$ is hydrogen or a straight-chained or branched alkyl group with 1-4 carbon atoms;

$R_3$ is a straight-chained or branched alkyl group with 1-3 carbon atoms; a hydroxyalkyl group with 2-3 carbon atoms; a phenyl group which can be mono- or di-substituted by chlorine, bromine, methyl or methoxy; a cyclohexyl group; or, a dialklaminoalkyl group wherein each alkyl group may contain from 1-3 carbon atoms; and, $R_4$ is hydrogen or a straight-chained or branched alkyl group with 1–3 carbon atoms;

as well as physiologically acceptable acid addition salts thereof.

2. Pyrrolidinones according to claim 1 wherein $R_1$ is a phenyl group, $R_2$ is hydrogen, $R_3$ is a phenyl group which is optionally substituted in the o- and/or p-position by chlorine, and $R_4$ is hydrogen.

3. In accordance with claim 1, 4-(p-Chlorophenylaminocarbonylaminomethyl)-1-benzylpyrrolidin-2-one.

4. Compounds in accordance with claims 1, 2, or 3 in their optically active form.

5. A pharmaceutical composition for treating cerebral insufficiently comprising a pharmaceutically acceptable carrier and an effective amount of a compound in accordance with claims 1, 2, or 3.

6. A method for treating conditions characterized by cerebral insufficiency or diminished cerebral performance which comprises administering, to a host requiring such treatment, a therapeutically effective amount of a compound in accordance with claims 1, 2, or 3.

* * * * *